United States Patent [19]
McClelland et al.

[11] Patent Number: 5,437,975
[45] Date of Patent: Aug. 1, 1995

[54] CONSENSUS SEQUENCE PRIMED POLYMERASE CHAIN REACTION METHOD FOR FINGERPRINTING GENOMES

[75] Inventors: Michael McClelland, Del Mar; John T. Welsh, Leucadia, both of Calif.

[73] Assignee: California Institute of Biological Research, La Jolla, Calif.

[21] Appl. No.: 661,591

[22] Filed: Feb. 25, 1991

[51] Int. Cl.⁶ .................. C12Q 1/68; C12P 19/34; C07H 21/04
[52] U.S. Cl. .................. 435/6; 435/91.2; 536/24.33; 935/78
[58] Field of Search .......... 435/91, 16, 91.2; 536/27, 124.33; 935/78

[56] References Cited

PUBLICATIONS

Nelson et al., *PNAS* 86, 6686–6690 (1989).
Cinco et al., *FEMS Microbiol. Immunol.*, 47:511–514 (1989).
Fox, *Ann. Rev. Genet.*, 21:67–91 (1987).
Giroux et al., *J. Bacteriol.*, 170:5601–5606 (1988).
Jeffreys et al., *Nature*, 316:76–79 (1985).
Jinks-Robertson et al., "E. coli and S. typhimurium Neidhardt ed., American Society for Microbiology Press", Washington, D.C, pp. 1358–1385 (1987).
Julier et al., *Proc. Natl. Acad. Sci. USA*, 87:4585–4589 (1990).
McBride et al., *Genomics*, 5:561–573 (1989).
Ohyama et al., *Nature*, 322:572–574 (1986).
Rogers et al., *Israel J. Med. Sci.*, 20:768–772 (1984).
Vold, *Microbiol. Rev.*, 49:71–80 (1985).
Welsh et al., *Nucl. Acids Res.*, 18:7213–7218 (1990).

Primary Examiner—Margaret Parr
Assistant Examiner—Kenneth R. Horlick
Attorney, Agent, or Firm—Pennie & Edmonds

[57] ABSTRACT

A rapid method for generating a set of discrete DNA amplification products characteristic of a genome as a "fingerprint" for typing the genome comprises the steps of: forming a polymerase chain reaction (PCR) admixture by combining, in a PCR buffer, genomic DNA and at least one structural RNA consensus primer, and subjecting the PCR admixture to a plurality of PCR thermocycles to produce a plurality of DNA segments, thereby forming a set of discrete DNA amplification products. The method is known as the consensus sequence primed polymerase chain reaction (CP-PCR) method and is suitable for the identification of bacterial species and strains, including Staphylococcus and Streptococcus species, mammals and plants. The method of the present invention can identify species rapidly, using only a small amount of biological material, and does not require knowledge of the nucleotide sequence or other molecular biology of the nucleic acids of the organisms to be identified. Only one primer sequence is required for amplification and/or identification. The method can also be used to generate detectable polymorphisms for use in genetic mapping of animals and humans.

4 Claims, 3 Drawing Sheets

FIG.1a
FIG.1b
FIG.1c
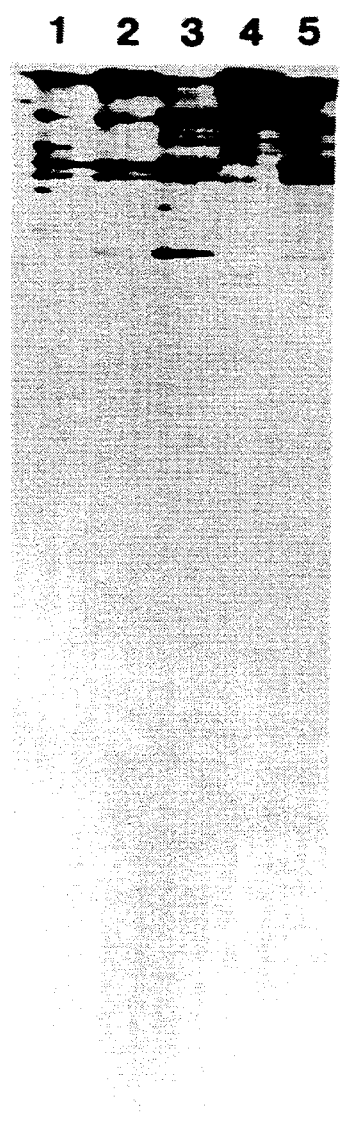
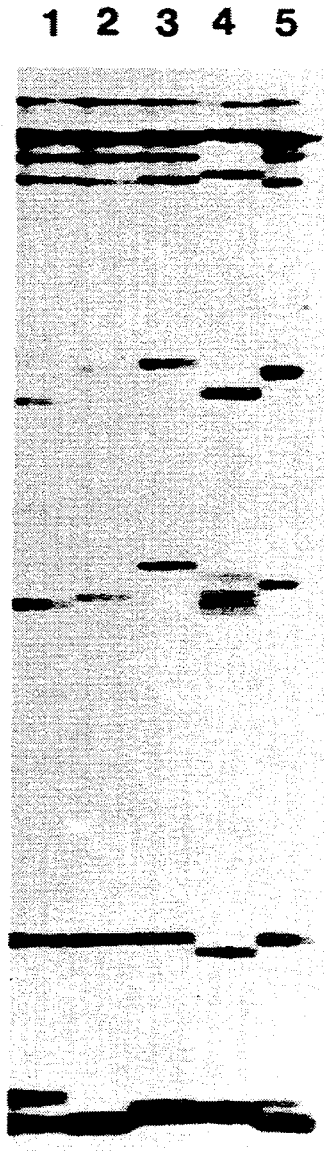

CONSENSUS SEQUENCE PRIMED POLYMERASE CHAIN REACTION METHOD FOR FINGERPRINTING GENOMES

FIELD OF THE INVENTION

This invention is directed toward a method of identifying segments of nucleic acid characteristic of a particular genome by generating a set of discrete DNA amplification products characteristic of the genome. This set of discrete DNA products can generate a fingerprint that can be used to identify the genome.

BACKGROUND OF THE INVENTION

For many purposes, it is important to be able to identify the species to which an organism belongs rapidly and accurately. Such rapid identification is necessary for pathogens such as viruses, bacteria, protozoa, and multicellular parasites, and assists in diagnosis and treatment of human and animal disease, as well as studies in epidemiology and ecology. In particular, because of the rapid growth of bacteria and the necessity for immediate and accurate treatment of diseases caused by them, it is especially important to have a fast method of identification.

Traditionally, identification and classification of bacterial species has been performed by study of morphology, determination of nutritional requirements or fermentation patterns, determination of antibiotic resistance, comparison of isoenzyme patterns, or determination of sensitivity to bacteriophage strains. These methods are time-consuming, typically requiring at least 48 to 72 hours, often much more. Other more recent methods include the determination of RNA sequences (Woese, in "Evolution in Procaryotes" (Schleifer and Stackebrandt, Eds., Academic Press, London, 1986)), the use of strain-specific fluorescent oligonucleotides (DeLong et al., Science 243, 1360-1363 (1989); Amann et al., J. Bact. 172, 762-770 (1990)), and the polymerase chain reaction (PCR) technique (U.S. Pat. Nos. 4,683,195 and 4,683,202 to Mullis et al.; Mullis & Faloona, Methods Enzymol. 154, 335-350 (1987)).

In addition, DNA markers genetically linked to a selected trait can be used for diagnostic procedures. The DNA markers commonly used are restriction fragment length polymorphisms (RFLPs). Polymorphisms useful in genetic mapping are those polymorphisms that segregate in populations. Traditionally, RFLPs have been detected by hybridization methodology (e.g. Southern blot), but such techniques are time-consuming and inefficient. Alternative methods include assays for polymorphisms using PCR.

The PCR method allows amplification of a selected region of DNA by providing two DNA primers, each of which is complementary to a portion of one strand within the selected region of DNA. These primers are used to hybridize to the separated strands within the region of DNA sought to be amplified, forming DNA molecules that are partially single-stranded and partially double-stranded. The double-stranded regions are then extended by the action of DNA polymerase, forming completely double-stranded molecules. These double-stranded molecules are then denatured and the denatured single strands are rehybridized to the primers. Repetition of this process through a number of cycles results in the generation of DNA strands that correspond in sequence to the region between the originally used primers. Specific PCR primer pairs can be used to identify genes characteristic of a particular species or even strain. PCR also obviates the need for cloning in order to compare the sequences of genes from related organisms, allowing the very rapid construction of phylogenies based on DNA sequence. For epidemiological purposes, specific primers to informative pathogenic features can be used in conjunction with PCR to identify pathogenic organisms.

Although PCR is a very powerful method for amplifying DNA, conventional PCR procedures require the use of at least two separate primers complementary to specific regions of the genome to be amplified. This requirement means that primers cannot be prepared unless the target DNA sequence information is available, and the primers must be "custom built" for each location within the genome of each species or strain whose DNA is to be amplified.

Although the newer methods have advantages over previous methods for genome identification, there is still a need for a rapid, simple method that can be applied to any species for which DNA can be prepared and that does not require reagents that are specific for each species or knowledge of the DNA sequence of the isolate being identified. It is also desirable that such a method be capable of identifying a species from a relatively small quantity of biological material. Additionally, it is highly desirable that such a method is also capable of generating polymorphisms useful in genetic mapping, especially of eukaryotes.

In addition to identification of related plant, animal and bacteria species, DNA segments or "markers" may be used to construct human genetic maps for genome analysis. Goals for the present human genome project include the production of a genetic map and an ordered array of clones along the genome. Using a genetic map, inherited phenotypes such as those that cause genetic diseases, can be localized on the map and ultimately cloned. The neurofibromatosis gene is a recent example of this strategy (Xu et al., Cell 62:599-608 (1990)). The genetic map is a useful framework upon which to assemble partially completed arrays of clones. In the short term, it is likely that arrays of human genomic clones such as cosmids or yeast artificial chromosomes (YACs, Burke et al., Science 236:806-812 (1987)) will form disconnected contigs that can be oriented relative to each other with probes that are on the genetic map or the in situ map (Lichter et al., Science 24:64-69 (1990)), or both. The usefulness of the contig map will depend on its relation to interesting genes, the locations of which may only be known genetically. Similarly, the restriction maps of the human genome generated by pulsed field electrophoresis (PFE) of large DNA fragments, are unlikely to be completed without the aid of closely spaced markers to orient partially completed maps. Thus, a restriction map and an array of clones covering an entire mammalian genome, for example the mouse genome, is desirable.

Recently, RFLPs that have Variable Number Tandem Repeats (VNTRs) have become a method of choice for human mapping because such VNTRs tend to have multiple alleles and are genetically informative because polymorphisms are more likely to be segregating within a family. The production of fingerprints by Southern blotting with VNTRs (Jeffreys et al., Nature 316:76-79 (1985)) has proven useful in forensics. There are two classes of VNTRs; one having repeat units of 9 to 40 base pairs, and the other consisting of minisatellite DNA with repeats of two or three base pairs. The longer VNTRs have tended to be in the proterminal regions of autosomes. VNTR consensus sequences may be used to display a fingerprint. VNTR fingerprints have been used to assign polymorphisms in the mouse (Julier et al., Proc. Natl. Acad. Sci. USA, 87:4585-4589 (1990)), but these polymorphisms must be cloned to be of use in application to restriction mapping or contig assembly. VNTR probes are useful in the mouse because a large number of crosses are likely to be informative at a particular position.

The mouse offers the opportunity to map in interspecific crosses which have a high level of polymorphism relative to most other inbred lines. A dense genetic map of DNA markers would facilitate cloning genes that have been mapped genetically in the mouse. Cloning such genes would be aided by the identification of very closely linked DNA polymorphisms. About 3000 mapped DNA polymorphisms are needed to provide a good probability of one polymorphism being within 500 kb of the gene. To place so many DNA markers on the map it is desirable to have a fast and cost-effective genetic mapping strategy.

SUMMARY OF THE INVENTION

Accordingly, the methods of the present invention, referred to herein as consensus sequence primed polymerase chain reaction or "CP-PCR" fingerprinting, provides a distinctive variation of the PCR technique by employing "consensus" sequence polynucleotide primers as defined herein. We have unexpectedly found that the use of at least one consensus primer, preferably a structural RNA consensus primer, in a standard PCR amplification procedure reproducibly generates specific discrete products that can be resolved into a manageable number of individual bands providing a species "fingerprint". The CP-PCR method is suitable for the rapid identification and classification of organisms throughout the plant, prokaryotic or eukaryotic kingdoms and for the generation of polymorphisms suitable for genetic mapping of eukaryotes. Only a small sample of biological material is needed, and knowledge of the target DNA sequence to be identified is not required. In addition, reagents specific for a given species are not required.

In general, CP-PCR is a method for generating a set of discrete DNA products ("amplification products") characteristic of a genome by priming target nucleic acid obtained from a genome with at least one single-stranded primer to form primed nucleic acid. The primed nucleic acid is then amplified by performing at least one cycle of polymerase chain reaction (PCR) amplification, and preferably at least 10 cycles, of PCR amplification to generate a set of discrete DNA amplification products characteristic of the genome.

The genome to which the CP-PCR method is applied can be a viral genome; a bacterial genome, including Staphylococcus and Streptococcus; a plant genome, including rice, maize, or soybean; or an animal genome, including a human genome. It can also be a genome of a cultured cell line. The cultured cell line can be a chimeric cell line with at least one human chromosome in a non-human background i.e., a hybrid cell line.

The CP-PCR method can be used to identify an organism as a species of a genus of bacteria, for example, Staphylococcus, from a number of different species. Similarly, the method can be used to determine the strain to which an isolate of the genus Streptococcus belongs, by comparing the DNA amplification products produced by CP-PCR for the isolate to the patterns produced from known strains with the same primer.

The CP-PCR method can also be used to verify the assignment of a bacterial isolate to a species by comparing the CP-PCR fingerprint from the isolate with the CP-PCR fingerprints produced by known bacterial species with the same primer. For this application, the primer is chosen as described herein to maximize interspecific difference of the discrete DNA amplification products.

The target nucleic acid of the genome can be DNA, RNA or polynucleotide molecules. If the CP-PCR method is used to characterize RNA, the method also preferably includes the step of extending the primed RNA with an enzyme having reverse transcriptase activity to produce a hybrid DNA-RNA molecule, and priming the DNA of the hybrid with an arbitrary single-stranded primer. In this application, the enzyme with reverse transcriptase activity can be avian myeloblastosis virus reverse transcriptase or Moloney leukemia virus reverse transcriptase.

The discrete DNA amplification products produced by the CP-PCR method can be manipulated in a number of ways. For example, they can be separated in a medium capable of separating DNA fragments by size, such as a polyacrylamide or agarose gel, in order to produce a fingerprint of the amplification products as separated bands. Additionally, at least one separated band can be isolated from the fingerprint and reamplified by conventional PCR. The isolated separated band can also be cleaved with a restriction endonuclease. The reamplified fragments can then be isolated and cloned in a bacterial host. The isolated band or reamplified fragments can be sequenced. These methods are particularly useful in the detection and isolation of DNA sequences that represent polymorphisms differing from individual to individual of a species.

The ability of the CP-PCR method to generate polymorphisms makes it useful, as well, in the mapping and characterization of eukaryotic genomes, including plant genomes, animal genomes, and the human genome. These polymorphisms are particularly useful in the generation of linkage maps and can be correlated with RFLPs and other markers.

Consensus primers, particularly structural RNA consensus primers are also contemplated, as are kits containing the primers in combination with control genomic DNA for typing isolated genomes.

BRIEF DESCRIPTION OF THE DRAWINGS

In the drawings forming a portion of this disclosure:

FIG. 1 shows the CP-PCR patterns produced by using isolates representing five different species of Staphylococcus, and illustrates the differences apparent between species, as described in Example 2. PCR was performed using the primers T5A in group a, T3A in group b, or T5A plus T3A in group c, at 50° C. Each numbered lane consists of three adjacent lanes having 80, 16 or 3.2 ng of template. Lane 1: S. haemolyticus CC 12J2. Lane 2: S. hominis 27844. Lane 3: S. warneri CPB10E2. Lane 4: S. cohnni JL 143. Lane 5: S. aureus ISP-8.

DETAILED DESCRIPTION OF THE INVENTION

Figure 2:
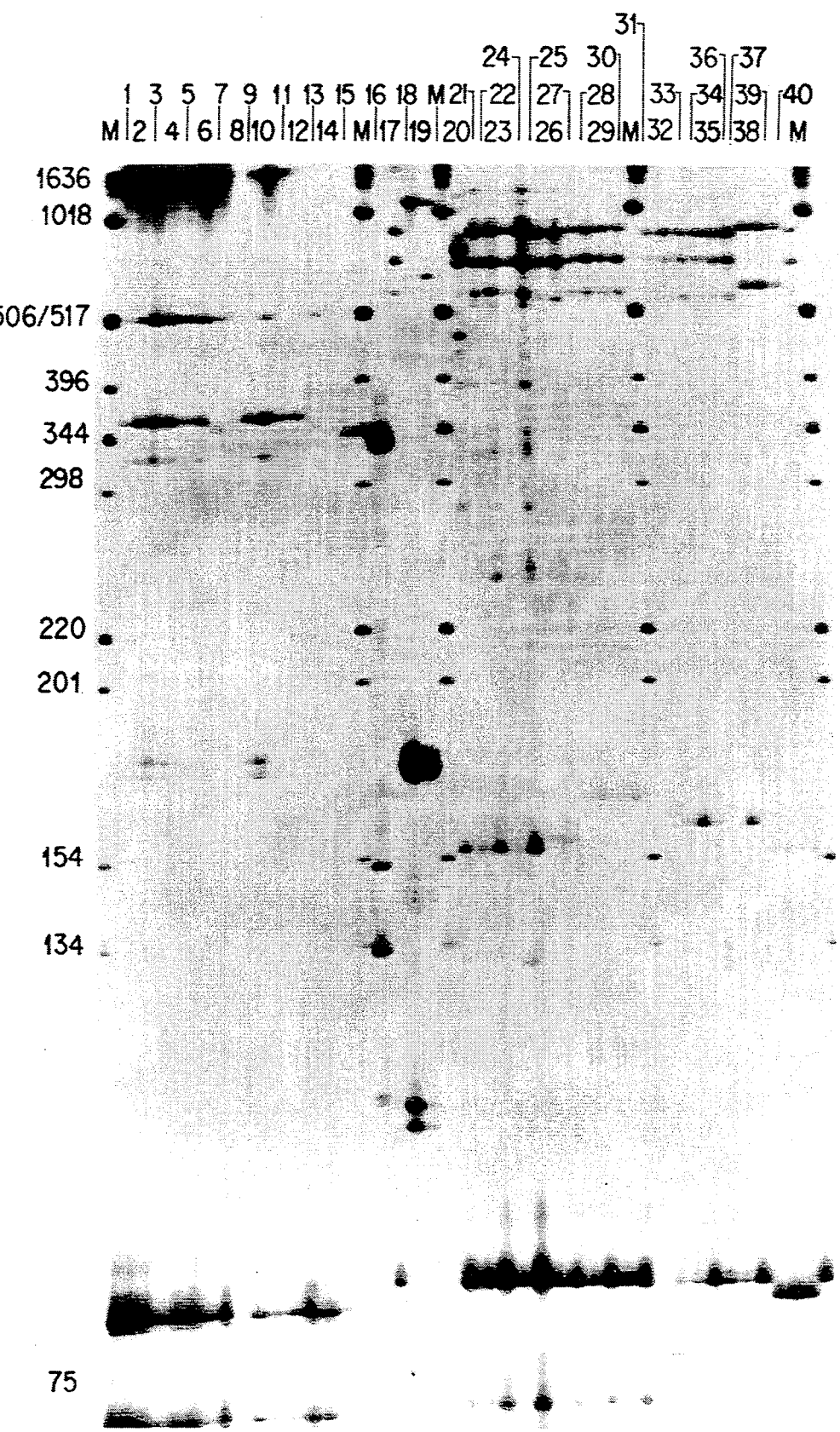
FIG. 2 shows the CP-PCR patterns produced by using forty strains of bacteria from three different genera, and illustrates the differences detectable between the strains and the general similarity of the patterns from the same species, as described in Example 2. PCR was performed using the primers T5A plus T3A at 50° C. with 100 ng of template. The templates in lanes 1 to 17 contain Streptococcus DNAs. Lanes 18 and 19 contain Enterococcus DNAs. Lanes 20 to 40 contain Staphylococcus DNAs. See Table 1 for the strains used in each lane.

In order that the invention herein described may be more fully understood, the following detailed description is set forth.

This invention relates to a method for generating a set of discrete DNA amplification products characteristic of a genome. This set of discrete DNA amplification products can be resolved by techniques such as gel electrophoresis, producing a distinctive pattern, known as a "fingerprint", that can be used to identify the genome. This method uses a distinctive and novel variation of the polymerase chain reaction (PCR) technique that employs one or more consensus primers based on a consensus sequence described herein and is therefore designated the "consensus sequence primed polymerase chain reaction" ("CP-PCR") method.

I. THE GENERAL METHOD

In general, the method of the invention involves the following steps:
(1) rendering target nucleic acids of the genome accessible to priming;
(2) priming the target nucleic acids of the genome with a preselected single-stranded consensus sequence primer to form primed nucleic acids;
(3) performing a number of cycles of PCR on the primed nucleic acids to generate a set of discrete amplification products; and
(4) if the discrete DNA amplification products are to be used for the identification of a genome, comparing the amplification products with those produced from nucleic acids obtained from genomes of known species.

Alternatively, the amplification products produced by the invention can be used to assemble genetic maps for genome analysis.

Each of these steps is discussed in detail below.

A. Selection of Genome

The method of the present invention is particularly well suited to the generation of discrete DNA amplification products from nucleic acids obtained from genomes of all sizes from $5 \times 10^4$ nucleotide bases (viruses) to $3 \times 10^9$ bases and greater (animals and plants).

"Nucleic acids" as that term is used herein means that class of molecules including single-stranded and double-stranded deoxyribonucleic acid (DNA), ribonucleic acid (RNA) and polynucleotides.

The CP-PCR method can be applied to such economically important plants as rice, maize, and soybean. It can also be applied to the human genome and to the genome of a cultured cell line. The cultured cell line can be chimeric with at least one human chromosome in an otherwise non-human background. The non-human background can be rodent, such as mouse or Chinese hamster.

As described in Example 2, infra, the DNA amplification products can be used to determine that an unidentified sample of an organism such as from a bacterium belongs to the genus Staphylococcus and can be used further to determine to which species and/or strain of that genus the organism belongs.

B. Rendering the Nucleic Acids of the Genome Accessible to Priming

"Genomic DNA" is used in an art recognized manner to refer to a population of DNA that comprises the complete genetic component of a species. Thus genomic DNA comprises the complete set of genes present in a preselected species. The complete set of genes in a species is also referred to as a genome. Depending on the species, genomic DNA can vary in complexity, and in number of nucleic acid molecules. In higher organisms, genomic DNA is organized into discrete nucleic acid molecules (chromosomes).

For species low in the evolutionary scale, such as bacteria, viruses, yeast, fungi and the like, a genome is significantly less complex than for a species high in the evolutionary scale. For example, whereas *E. coli* is estimated to contain approximately $2.4 \times 10^9$ grams per mole of haploid genome, man contains about $7.4 \times 10^{12}$ grams per mole of haploid genome.

Genomic DNA is typically prepared by bulk isolation of the total population of high molecular weight nucleic acid molecules present in a biological material derived from a single member of a species. Genomic DNA can be prepared from a tissue sample, from a whole organism or from a sample of cells derived from the organism.

Exemplary biological materials for preparing mammalian genomic DNA include a sample of blood, muscle or skin cells, tissue biopsy or cells cultured from tissue, methods for isolating high molecular weight DNA are well known. See, for example, Maniatis et al., in *Molecular Cloning: A Laboratory Manual*, Cold Spring Harbor Laboratory, New York (1982); and U.S. Pat. No. 4,800,159 to Mullis et al.

Rendering the nucleic acids of the genome accessible to priming requires that the nucleic acids be available for base-pairing by primers and that DNA polymerases and other enzymes that act on the primer-template complex can do so without interference. The nucleic acids must be substantially free of protein that would interfere with priming or the PCR process, especially active nuclease, as well as being substantially free of nonprotein inhibitors of polymerase action such as heavy metals.

A number of methods well-known in the art are suitable for the preparation of nucleic acids in a condition accessible to priming. Typically, such methods involve treatment of cells or other nucleic acid-containing structures, such as virus particles, with a protease such as proteinase K or pronase and a strong detergent such as sodium dodecyl sulfate ("SDS") or sodium lauryl sarcosinate ("Sarkosyl") to lyse the cells. This is followed by extraction with phenol and chloroform to yield an aqueous phase containing the nucleic acid. This nucleic acid is then precipitated with ethanol and redissolved as needed. (See Example 1, infra).

Alternatively, as where the genome is in bacteria, a small portion (~0.5 mm²) of a single bacterial colony can be removed with a 200-μL automatic pipette tip and suspended in 5 μL of TE (0.01M Tris-HCl, pH 8.0, 1 mM EDTA) in a plastic microfuge tube and boiled for 5 minutes. After the sample is boiled, the debris is pelleted by centrifugation. The CP-PCR method can then be performed directly on the nucleic acids present in the supernatant sample after appropriate dilution.

In some applications, it is possible to introduce samples such as blood or bacteria directly into the PCR protocol as described below without any preliminary step because the first cycle at 94° C. bursts the cells and inactivates any enzymes present.

C. Priming the Target Nucleic Acids

1. The Consensus Primer Sequence a. General Considerations

The sample of target nucleic acids is primed with a single-stranded primer. Individual single-stranded primers, pairs of single-stranded primers or a mixture of single-stranded primers can be used.

A primer for use in this inventions is a consensus sequence polynucleotide primer, or consensus primer. A consensus primer is a polynucleotide having a nucleotide sequence that comprises a region at its 3' terminus that is homologous to a consensus sequence derived from a family of related genes within a genome, or derived from related genes found in the genomes of different species. The related genes from which a consensus primer is derived are a class of genes that occur in the genome as a cluster within the genome.

Clusters of related genes are known to occur for a variety of gene families, any of which are suitable as a source of related genes for deriving a consensus primer for use in the present invention. Gene clusters are regions of a genome in which related genes are organized within a single nucleic acid molecule of the genome, i.e., are genetically linked. Gene clusters comprise two domains: (1) the nucleotide sequences that define each of the related genes that are members of the cluster, and (2) the nucleotide sequences that define the spacer region between each member of the related genes of the cluster. Whereas the related genes (members) of the cluster are conserved when compared at the level of sub-species, species, family, order or other division of evolutionary relatedness, the spacer region of a gene cluster is more variable in nucleotide sequence than the nucleotide sequence defining a member of a cluster.

Variability in the spacer regions of a gene cluster provides the polymorphisms that produce a fingerprint by the present methods which is characteristic of the organism being analyzed. Variability in spacer regions can be manifest by differences in actual sequence, by differences in spacer length between members of the cluster, and even by differences in overall organization of the members of a cluster.

Organization of related genes in a cluster can vary both in the linear order of the members of the cluster on the nucleic acid molecule defining the cluster and in the orientation of each member of the cluster relative to one another.

Typical and preferred gene clusters are the structural RNA families, namely the family of genes that encode transfer RNA (tRNA) molecules, and the family of genes that encode ribosomal RNA (rRNA) molecules known as 28s, 16s and 5s rRNA's. Other gene clusters are the linked genetic elements of an operon.

The tRNA gene cluster is particularly preferred and is exemplary of the general methods described herein.

Although the sequence of the primer can vary widely, so long as it comprises a consensus sequence at it's 3' termini, some guidelines to primer selection are found in Innis and Gelfand, "Optimization of PCRs," in *PCR Protocols: A Guide to Methods and Applications* (M. A. Innis, D. H. Gelfand, J. J. Sninsky and T. J. White, eds., Academic Press, New York, 1990), pp. 3–12, incorporated herein by this reference. Briefly, the primer typically has 50 to 60% G+C composition and is free of runs of three or more consecutive C's or G's at the 3'-end or of palindromic sequences, although having a (G+C)-rich region near the 3'-end may be desirable. These guidelines, however, are general and intended to be nonlimiting. Additionally, in many applications it is desirable to avoid primers with a T at the 3' end because such primers can prime relatively efficiently at mismatches, creating a degree of mismatching greater than desired, and affect the background amplification.

The CP-PCR method is based on the rationale that for any preselected gene cluster, which comprises at least two related and genetically linked genes, there is a spacer region between the linked genes which is variable and contains nucleotide sequence differences when compared to the same region from a different sub-species, species, genus, family or other evolutionary division of organisms having members of the gene cluster. The consensus primer is selected to amplify one or more specific primer extensions products that contain the nucleotide sequence of one or more of the spacer regions between two genes of a cluster.

The consensus primer amplifies DNA segments containing spacer regions because the primer is selected to provide a 3' terminus for primer extension that "points" the direction of primer extension across the spacer region. The consensus sequence of the primer is selected such that there is a degree of homology with a consensus region within the individual members of a gene cluster that the primers can be expected to anneal to many consensus sequences contained within a variety of the members of a gene cluster. Some of these will be within a few hundred basepairs of each other and on opposite strands thereby satisfying the requirements for PCR amplification. Thus, the sequences between these consensus sequence positions will be PCR amplifiable. The extent to which sequences amplify will depend on the efficiency of priming at each pair of primer annealing sites. Because the sequence of the primer is selected to contain some degree of homology with a consensus sequence with respect to the target nucleic acid sequence of the genome, a substantial degree of hybridization between the DNA strands of the primer and the target nucleic acids of the genome is expected to occur. "Substantial degree of hybridization" is defined herein to mean in the context of a primer extension reaction thermocycle in which primer annealing occurs, that the hybridizing conditions favor annealing of homologous nucleotide sequences under "high stringency conditions". In some embodiments, where less evolutionary relatedness is desired, the hybridizing conditions can be carried out under low stringency or intermediate stringency conditions so that up to 10% of the nucleotide bases of a primer sequence are paired with inappropriate (non-complementary) bases in the target nucleic acid, e.g. a guanine base in the primer is paired with an adenine base in the target nucleic acid.

As used herein, the phrase "internal mismatching" in its various grammatical forms refers to non-complementary nucleotide bases in the primer, relative to a template to which it is hybridized, that occur between the 5'-terminal most and 3'-terminal most bases of the primer that are complementary to the template. Thus, 5'-terminal and/or 3'-terminal non-complementary bases are not "internally mismatched" bases. A "substantial degree of "internal mismatching" is such that at least 6.5% of the nucleotide bases of the primer sequence are paired with inappropriate bases in the target nucleic acid.

In the CP-PCR method of the invention the genome may be primed with a single consensus primer, a combination of two or more primers or a mixture of heterogeneous primers, each individual primer in the mixture having a different, but related sequence. When a mixture of primers is used, some, but not all, of the primers can match more efficiently. An example of use of a mixture of primers is provided in Example 2, infra.

Preferably, the consensus primer is about 10 to about 50 nucleotide bases long, and more preferably, about 17 to about 40 bases long. In principle, the shorter the oligonucleotide, the more perfect a match must be in order to permit priming. The primer can be of any sequence so long as it comprises a consensus sequence as defined herein. The primer can have sequence redundancies reducing the occurrence of mismatches.

Preferably, both the template and the primer are DNA. The template can also be single-stranded RNA molecules, for example messenger RNA, in which case an enzyme with reverse transcriptase activity, such as avian myeloblastosis virus (AMV) reverse transcriptase or Moloney murine leukemia virus (Mo-MLV) reverse transcriptase, is used to generate a hybrid DNA-RNA molecule with an arbitrary primer or a poly T primer. The DNA strand of this hybrid DNA-RNA molecule is then used as the starting material for AP-PCR. Alternatively, the primer can also be a single-stranded ribonucleotide of the appropriate length, which is extended at its 3'-hydroxyl terminus by reverse transcriptase, forming a double-stranded molecule in which one strand is partially DNA and partially RNA.

b. Conserved Transfer RNA Primers

The gene clusters formed by tRNA genes provides a preferred family of related genes for practicing the methods of the present invention.

tRNA genes occur in multiple copies dispersed throughout the genome in most species and tend to be clustered. McBride et al, Genomics, 5:561-573 (1989). In E. coli, there is estimated to be at least 100 tRNA genes of which about 30 are mapped. Jinks-Robertson et al, in "E coli and S. typhimurium", Neidhardt, ed., ASM Press, Washington, pp. 1358-1385 (1989). About half of the mapped genes are in seven clusters of two to seven genes per cluster, with a spacing of genes being variable ranging from 10 to 200 basepairs. The genes are generally arranged in a head to tail fashion and are, at least in some cases, organized into operons. In Bacillus subtilis, Photobacterium phosphoreum and Spiroplasma the genes are more tightly clustered. See, Vold, Microbiol. Rev., 49: 71-90 (1985); Giroux et al, J. Bacteriol., 170: 5601-5606 (1988); and Rogers et al, Israel J. Med. Sci., 20: 768-772 (1984), respectively. For instance, in B. subtilis there are two main clusters consisting of 16 and 21 tRNA genes. One operon in P. phosphoreum has eight genes and five tRNA$^{Pro}$ pseudogenes, all in less than 1,500 base pairs. In the human nuclear genome there are estimated to be 1300 genes and a large number of tRNA pseudogenes. At least seven clusters are on seven different chromosomes. McBride et al, Genomics, 5: 561-573 (1989). However, in the few characterized cases in mammals, the tRNA genes are not in operons, being oriented in all possible directions within clusters.

Fungi, plants and animals have organelle genomes in addition to their nuclear genomes. Organelle genomes are much smaller than nuclear genomes but nevertheless encode tRNA genes for a more redundant genetic code. For example, the very small (circa 16,000 bp) animal mitochondrial DNA has 22 tRNA genes, some of which are closely spaced. Fox, Ann. Rev. Genet., 21:67-91 (1987).

Chloroplast and mitochondrial DNA from plants are generally more complex than those in animals and often have more tRNA genes. For instance, the 121,024 base pair chloroplast genome of liverwort has 36 tRNA genes, a few of which are clustered. The yeast mitochondrial genome has at least 25 tRNA genes in 78,000 base pairs. Ohyama et al, Nature, 322: 572-574 (1986).

Consensus tRNA primers for use in the present methods were developed using the known tRNA sequences available in nucleotide sequence databases. Presently, over 500 tRNA sequences are known.

Given the variability in tRNA gene sequences between isoacceptors from different species, and the even greater difference between tRNAs for different amino acids, a substantial universal consensus does not exist. However, a reasonable match with a fraction of all tRNAs can readily be devised. With this objective, it is possible to identify and produce consensus primers that have (a) at least a five base perfect match between the 3' end of the primer and many tRNA genes and (b) extensive homology in the rest of the primer with a number of different tRNA genes from a wide variety of sources.

A primer sequence is a consensus sequence if at least five nucleotides at the 3' end of the primer are a perfect match in homology to at least several members of a set of possible members of the family of genes in the cluster, together with extensive homology in the rest of the primer as described herein. Preferably, the match is to at least 10 percent of the members where the set comprises at least one tRNA gene for each natural amino acid (i.e., a set size of 21 tRNA genes). More preferably, the match is to at least 30 percent, and still more preferably at least 50 percent, of the members of a set comprising 21 members.

Because more than one possible nucleotide can reside at a position of a consensus sequence and satisfy the requirements above, one embodiment contemplates that a consensus sequence contains the most common nucleotide of the set at any given position or the next most common nucleotide of the set that occurs at that same position in excess of 10 percent, and more preferably 30 percent, of the members where the set comprises 21 members.

Alternatively, a tRNA consensus sequence can be defined in terms of a subset of tRNA genes, with the objective being to design a primer that produces a fingerprint that is more specific to a particular genome. In this case, the consensus can be limited to a family of tRNA genes for a particular amino acid, such as phenylalanine, i.e., tRNA-Phe, where the tRNA-Phe genes are from a single genome, or from a family of related species, or related genera.

In a preferred embodiment that is exemplary herein, a consensus sequence was developed by comparing the tRNA genes for a complete set of natural amino acids (21 members) from the genome of the bacteria Bacillus. Of importance is the fact that the consensus, although derived from Bacillus, produced consensus primers that would produce fingerprints in species of organisms across the kingdoms including plant, bacteria and animal. Thus, the selection of the consensus sequence is not critical to the general method of the present invention, so long as the sequence represents a consensus in the manner defined herein. However, the selection of a particular consensus sequence, and the extent of homology contained in the sequence will alter the particular fingerprint observed for a particular genome.

For example, using the known 21 Bacillus tRNA genes coding the 21 common amino acids, a consensus can be identified where 8 of the 21 tRNA genes exhibit a 5 base perfect match at the resulting consensus primer's 3' end. This primer, designated T5A, also has at least 10 of the remaining 19 nucleotide bases perfectly matched with those 8 tRNA genes.

Consensus primer T5A has the nucleotide base sequence shown in Table 1 and is derived from the complement of a consensus sequence at the 5' terminal region of the Bacillus tRNA genes. Therefor the consensus primer faces out from a tRNA gene in the 5' to 3' direction across a spacer region located upstream from any tRNA gene having a sequence match to which T5A can hybridize.

By "faces out" is meant, with respect to members of a gene cluster and the respective spacer region, that the 3' end of the primer, when hybridized to a consensus sequence region of a member of the gene cluster, provides an initiator 3' end for primer extension to pass into the spacer region and away from the interior of the member gene, i.e., the primer extension product extends "out" into the spacer rather than "in" into the member gene.

Consensus primers T5B, T3A and T3B were fashioned in a similar manner as above for T5A. Namely, tRNA genes were aligned for all 21 amino acid tRNA genes, and "best match" consensus sequences were developed.

T5B, like T5A, faces out and upstream from the 5' end of the consensus sequence, whereas T3A and T3B represent consensus sequences at the 3' end of the tRNA gene facing out and downstream from the 3' end of the tRNA gene and will primer extend across the spacer region downstream from a tRNA gene.

The sequences of the tRNA consensus primers T5A, T5B, T3A and T3B, respectively SEQ ID NOS 1-4, are shown in Table 1 below and are written in the direction of 5' to 3'.

TABLE 1

| T5A | 5'-AGTCCGGTGCTCTAACCAACTGAG- 3' |
| T5B | 5'-AATGCTCTACCAACTGAACT- 3' |
| T3A | 5'-GGGGGTTCGAATTCCCGCCGGCCCCA- 3' |
| T3B | 5'-AGGTCGCGGGTTCGAATCC-3' |

Given that there are one hundred or more divergent tRNA genes in a typical genome, there are likely to be many matches for the above primers and these will vary from almost perfect to rather poor matches depending on the consensus sequence target to which the primers are hybridized. Other consensus sequences can be similarly derived by comparing the tRNA gene families of other species, both within the family of genes for a given species or by comparison to tRNA genes in different species.

The consensus primers shown on Table 1 are particularly preferred and are used as exemplary of the methods of the present invention.

However, other consensus tRNA primers can be designed so long as the resulting sequence contains a minimum of a three base perfect match, and preferably at least a 5 base perfect match, at the 3' end of the consensus primer, together with a minimum of at least a 50 percent match with the next 15 bases of the primer adjacent to the perfect match region of the primer, when the consensus sequence is compared to at least ten of the 21 amino acid tRNA genes for a given genome.

In one embodiment, a consensus tRNA primer can have a nucleotide sequence at its 3'-terminus corresponding to the sequence 5'-CTGAG-3', 5'-GAACT-3', 5'-CCCCA-3', or 5'-AATCC-3', which sequences are derived from the tRNA primers utilized in Example 2. These consensus primers have a length of at least fifteen nucleotides, and additionally have about 30 percent homology, and preferably at least fifty percent homology, to a consensus tRNA sequence in the fifteen nucleotides located at the 3'terminus of the primer.

A consensus primer can also be a nucleotide sequence based on another consensus primer of this invention but being progressively truncated at the 5' end.

A single tRNA consensus primer can provide the requisite "pair" of primers for a PCR amplification product to form in those cases where separate primer molecules having the same consensus sequence independently hybridize to opposite polarity strands of the target genome. This independent hybridization is possible for several reasons. First, the target genome can contain tRNA genes in opposite relative orientations on the genome so that two tRNA genes each provide a consensus sequence such that the resulting hybridized primers "face out" from their respective tRNA genes and at the same time "face toward" each other. Second, both the 5' and 3' ends of tRNA gene exhibit some degree of homology, which is well known and contributes to the classical "cloverleaf" structure of a tRNA molecule. Thus, the same homology that allows for the 5' and 3' ends of a tRNA molecule to self-hybridize is available to hybridize to a consensus primer selected to have homology to both a 3' and 5' end of the tRNA gene.

Exemplary of single consensus tRNA primers useful to produce a characteristic fingerprint are the primers T5A and T3A, each described in Example 1.

The tRNA gene cluster, as described above, is a preferred gene cluster for practicing the fingerprint characterization methods described herein. Due to the nature of evolutionary genetics and the size and organization of tRNA gene clusters, tRNA polymorphisms observed by the present fingerprinting methods are variances due to differences in spacer length and sequence content rather than differences in overall cluster organization.

The results using consensus tRNA primers indicates that the fingerprint method of CP-PCR is most useful to make identification of a particular genus, although in some cases consensus tRNA primers can be used to distinguish species. See, for example FIG. 1.

c. Conserved Ribosomal RNA Primers

The gene cluster formed by the ribosomal RNA (rRNA) gene family is less complex than the tRNA gene cluster (having fewer members) and is considerably more well conserved than the tRNA gene cluster both at the level of organization of the cluster, and at the level of the sequences within the rRNA genes. The rRNA cluster is comprised of three major species, the 28s, the 16s and the 5s rRNA genes.

The "consensus" in the case of the rRNA cluster is not a similar nucleotide sequence found that is common to the members of the cluster as was the case for the tRNA gene family members. Rather, the "consensus" is found between species. For example, the 5' end of the 28s rRNA gene is evolutionarily conserved between all genera across the bacterial kingdom to the extent that consensus primers can be defined from the 28s rRNA gene that produce family specific, order specific and even kingdom specific fingerprints when using consensus rRNA primers in the present invention.

Therefore, polymorphisms observed using consensus rRNA primers are at the level of family, order and higher evolutionary categories than the polymorphisms observed for consensus tRNA primers. This is primarily due to the fact that rRNA gene clusters are smaller and more evolutionarily conserved than tRNA clusters.

d. Use of Mixtures of Primers

As discussed above, mixtures of heterogeneous primers can also be used, with each primer in the mixture having a different sequence. The individual primers in the mixture can all be the same length. Preferably, primers are constructed to avoid self-priming internally and the creation of artifacts.

A heterogeneous mixture of primers may contain some primers that match with the consensus sequences on target nucleic acids in a manner that provides a more distinct fingerprint. The use of such primers may allow the initial priming steps to be performed at a higher temperature (higher stringency) or might allow a consistency of pattern over a wider range of template concentrations.

When combinations of two or more individual primers are used, the primers are used simultaneously in the same CP-PCR reaction. These combinations provide a very different pattern from that produced by each primer alone. See, for example, the difference observed in FIG. 1 between group a, group b and group c utilizing one, one, and two primers, respectively. Therefore, a combination of primers provides a different fingerprint than is generated by using each individual primer alone. When primers are used in such combinations, only primer pairs that do not produce a primer artifact can be used.

In one embodiment, a mixture of primers comprises two or more primers where the nucleotide sequences of each primer are substantially identical, except that a few nucleotide bases differ at a single position or at two positions. These mixtures contain consensus primers that each individually exhibit consensus matches with different subsets of members of a gene cluster. Thus, the use of two primers produces a distinct pattern that is typically more complex and therefore more characteristic of any given genome than the use of either primer alone.

2. Concentration of Primer and Template

The quantity of the nucleic acid genome used in the CP-PCR amplification depends on the complexity of the particular genome used. Simple genomes, such as bacterial genomes have a genome size of less than about 5 million base pairs (5 megabases). Complex genomes, such as sativa species (rice) have a genome size of about 700–1000 megabases. Other complex genomes such as maize or humans have a genome size of about 3000 megabases.

The amount of simple genome nucleic acid used as template is from about 10 pg to about 250 ng, preferably from about 30 pg to about 7.5 ng. Most preferred is an amount of simple genome nucleic acid template of about 1 ng.

The amount of nucleic acid of a complex genome used as a template is from about 250 ng to about 0.8 ng. More preferably, the amount of nucleic acid of a complex genome used as template is from about 51 ng to about 0.8 ng. Most preferred, are amounts complex genome nucleic acid template of about 50 ng to about 10 ng.

The priming step is carried out as part of the PCR amplification process, and the conditions under which it is performed are discussed below under "Performance of PCR."

D. Performance of PCR

In one embodiment, the present invention utilizes an amplification method where the single-stranded template is hybridized with a primer or primers to form a primer-template hybridization product or products. A hybridization reaction admixture is prepared by admixing effective amounts of a primer, a template nucleic acid and other components compatible with a hybridization reaction. Templates of the present methods can be present in any form, with respect to purity and concentration, compatible with the hybridization reaction.

The hybridization reaction mixture is maintained under hybridizing conditions for a time period sufficient for the primer(s) to hybridize to the templates to form a hybridization product, i.e., a complex containing primer and template nucleic acid strands.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow the primer(s) to anneal with the template, typically to form a nucleic acid duplex. Such time, temperature and pH conditions required to accomplish hybridization depend, as is well known in the art, on the length of the primer to be hybridized, the degree of complementarity between the primer and the template, the guanidine and cytosine content of the polynucleotide the stringency of hybridization desired, and the presence of salts or additional reagents in the hybridization reaction admixture as may affect the kinetics of hybridization. Methods for optimizing hybridization conditions for a given hybridization reaction admixture are well known in the art.

The term "primer" as used herein refers to a polynucleotide, whether purified from a nucleic acid restriction digest or produced synthetically which is capable of acting as a point of initiation of synthesis when placed under conditions in which synthesis of a primer extension product which is complementary to a template is induced, i.e., in the presence of nucleotides and an agent for polymerization such as DNA polymerase, reverse transcriptase and the like, and at a suitable temperature and pH.

The primer must be sufficiently long to prime the synthesis of extension products in the presence of the agents for polymerization. The exact lengths of the primers will depend on many factors, including temperature and the source of primer. For example, depending on the complexity of the template sequence, a polynucleotide primer typically contains from about 8 to about 30 or more nucleotides, although it can contain fewer nucleotides. As few as 8 nucleotides in a polynucleotide primer have been reported as effective for use. Studier et al., *Proc. Natl. Acad. Sci. USA*, 86:6917–21 (1989). Short primer molecules generally require lower temperatures to form sufficiently stable hybridization complexes with template to initiate primer extension.

In some cases, the primers used herein are selected to be "substantially" complementary to the different strands of each specific sequence to be synthesized or amplified. This means that the primer must contain at its 3' terminus a nucleotide sequence sufficiently complementary to nonrandomly hybridize with its respective template. Therefore, the primer sequence may not reflect the exact sequence of the template. For example, a non-complementary polynucleotide can be attached to the 5' end of the primer, with the remainder of the primer sequence being substantially complementary to the strand. Such noncomplementary polynucleotides might code for an endonuclease restriction site or a site for protein binding. Alternatively, noncomplementarity bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Sommer et al., *Nuc. Acid Res.*, 17:6749 (1989), reports that primers having as little a 3 nucleotide exact match at the 3' end of the primer were capable of specifically initiating primer extension products, although less non-specific hybridization occurs when the primer contains more nucleotides at the 3' end having exact complementarity with the template sequence. Therefore, a substantially complementary primer as used herein must contain at its 3' end at least 3 nucleotides having exact complementarity to the template sequence. A substantially complementary primer preferably contains at least 8 nucleotides, more preferably at least 18 nucleotides, and still more preferably at least 24 nucleotides, at its 3' end having the aforementioned complementarity. Still more preferred are primers whose entire nucleotide sequence has exact complementarity with the template sequence.

The choice of a primer's nucleotide sequence depends on factors such as the distance from the region coding for the desired specific nucleic acid sequence present in a nucleic acid of interest and its hybridization site on the nucleic acid relative to any second primer to be used.

The primer is preferably provided in single-stranded form for maximum efficiency, but may alternatively be double-stranded. If double-stranded, the primer is first treated to separate its strands before being used to prepare extension products. preferably, the primer is a oligodeoxyribonucleotide.

Primers can be prepared by a variety of methods including de novo chemical synthesis and derivation of nucleic acid fragments from native nucleic acid sequences existing as genes, or parts of genes, in a genome, plasmid, or other vector, such as by restriction endonuclease digest of larger double-stranded nucleic acids and strand separation or by enzymatic synthesis using a nucleic acid template.

De novo chemical synthesis of a primer can be conducted using any suitable method, such as, for example, the phosphotriester or phosphodiester methods. See Narang et al., *Meth. Enzymol.*, 68:90 (1979); U.S. Pat. No. 4,356,270; Itakura et al., *Ann. Rev. Biochem.*, 53:323–56 (1989); and Brown et al., *Meth. Enzymol.*, 68:109 (1979).

Derivation of a primer from nucleic acids involves the cloning of a nucleic acid into an appropriate host by means of a cloning vector, replication of the vector and therefore multiplication of the amount of the cloned nucleic acid, and then the isolation of subfragments of the cloned nucleic acids. For a description of subcloning nucleic acid fragments, see Maniatis et al., *Molecular Cloning: A Laboratory Manual*, Cold Spring Harbor Laboratory, pp 390–401 (1982); and see U.S. Pat. Nos. 4,416,988 and 4,403,036.

The primed template is used to produce a strand of nucleic acid having a nucleotide sequence complementary to the template, i.e., a template-complement.

The template is subjected to a first primer extension reaction by treating (contacting) the template with a (first) primer. The primer is capable of initiating a primer extension reaction by non-randomly hybridizing (annealing) to a template nucleotide sequence, preferably at least about 8 nucleotides in length and more preferably at least about 20 nucleotide in length. This is accomplished by mixing an effective amount of the primer with the template and an effective amount of nucleic acid synthesis inducing agent to form a primer extension reaction admixture. The admixture is maintained under polynucleotide synthesizing conditions for a time period, which is typically predetermined, sufficient for the formation of a primer extension reaction product.

The primer extension reaction is performed using any suitable method. Generally polynucleotide synthesizing conditions are those wherein the reaction occurs in a buffered aqueous solution, preferably at a pH of 7–9, most preferably about 8. Preferably, a molar excess (for genomic nucleic acid, usually about $10^6:1$ primer:template) of the primer is admixed to the buffer containing the template strand. A large molar excess is preferred to improve the efficiency of the process. For polynucleotide primers of about 20 to 25 nucleotides in length, a typical ratio is in the range of 50 ng to 1 ug, preferably 250 ng, of primer per 100 ng to 500 ng of mammalian genomic DNA.

The deoxyribonucleotide triphosphates (dNTPs) dATP, dCTP, dGTP, and dTTP are also admixed to the primer extension reaction admixture in amounts adequate to support the synthesis of primer extension products, and depends on the size and number of products to be synthesized. The resulting solution is heated to about 90° C.–100° C. for about 1 to 10 minutes, preferably from 1 to 4 minutes. After this heating period the solution is allowed to cool to room temperature, which is preferable for primer hybridization. To the cooled mixture is added an appropriate agent for inducing or catalyzing the primer extension reaction, and the reaction is allowed to occur under conditions known in the art. The synthesis reaction may occur at from room temperature up to a temperature above which the inducing agent no longer functions efficiently. For example, if DNA polymerase is used as inducing agent, the temperature is generally no greater than about 40° C. unless the polymerase is heat-stable.

The inducing agent may be any compound or system which will function to accomplish the synthesis of primer extension products, including enzymes. Suitable enzymes for this purpose include, for example, *E. coli,* DNA polymerase I, Klenow fragment of *E. Coli* DNA polymerase I, T4 DNA polymerase, T7 DNA polymerase, recombinant modified T7 DNA polymerase described by Tabor et al., U.S. Pat. Nos. 4,942,130 and 4,946,786, other available DNA polymerases, reverse transcriptase, and other enzymes, including heat-stable enzymes, which will facilitate combination of the nucleotides in the proper manner to form the primer extension products which are complementary to each nucleic acid strand.

Heat-stable DNA polymerases are particularly preferred as they are stable in a most preferred embodiment in which PCR is conducted in a single solution in which the temperature is cycled. Representative heat-stable polymerases are the DNA polymerases isolated from *Bacillus stearothermophilus* (Bio-Rad), *Thermus thermophilous* (FINZYME, ATCC #27634), *Thermus species* (ATCC #31674), *Thermus aquaticus* strain TV 11518 (ATCC #25105), *Sulfolobus acidocaldarius,* described by Bukhrashuili et al, *Biochem. Biophys. Acta,* 1008: 102–7 (1990) and by Elie et al, *Biochem. Biophys. Acta,* 951:261–7 (1988), and *Thermus filiformis* (ATCC #43280). Particularly preferred is Taq DNA polymerase available from a variety of sources including Perkin-Elmer-Cetus, (Norwalk, Conn.), Promega (Madison, Wis.) and Stratagene (La Jolla, Calif.), and AmpliTaq ™ DNA polymerase, a recombinant *Thermus aquaticus* Taq DNA polymerase available from Perkin-Elmer-Cetus and described in U.S. Pat. No. 4,889,818.

Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The primer extension reaction product is then subjected to a second primer extension reaction by treating it with a second polynucleotide primer having a preselected nucleotide sequence. The second primer is capable of initiating the second reaction by hybridizing to a nucleotide sequence, preferably at least about 8 nucleotides in length and more preferably at least about 20 nucleotides in length, found in the first product. This is accomplished by mixing the second primer, preferably a predetermined amount thereof, with the first reaction product, preferably a predetermined amount thereof, to form a second primer extension reaction admixture. The admixture is maintained under polynucleotide synthesizing conditions for a time period, which is typically predetermined, sufficient for the formation of a second primer extension reaction product.

In preferred strategies, the first and second primer extension reactions are the first and second primer extension reactions in a polymerase chain reaction (PCR).

PCR is carried out by simultaneously cycling, i.e., performing in one admixture, the above described first and second primer extension reactions, each cycle comprising polynucleotide synthesis followed by separation of the double-stranded polynucleotides formed.

PCR is preferably performed using a distinguishable variation of the standard protocol as described in U.S. Pat. Nos. 4,683,192, 4,683,202, 4,800,159 and 4,965,188 to Mullis et al., and 4,889,818 to Gelfand et al., and in the Innis & Gelfand reference described above, employing only one primer. The principles of the PCR process have been described under "Background of the Invention," supra. Typically, the DNA polymerase used in CP-PCR is the thermostable DNA polymerase purified from *Thermus aquaticus* and known as Taq I. However, other heat-stable DNA polymerases can be used.

A PCR thermocycle is the changing of a PCR admixture from a first temperature to another temperature and then back to the first temperature. That is, it is cycling the temperature of the PCR admixture within (up and down through) a range of temperatures. Typically, the change in temperature is not linear with time, but contains periods of slow or no temperature change and periods of rapid temperature change, the former corresponding to, depending on the temperature, a hybridization (annealing), primer extension or denaturation phase, and the later to temperature transition phases. Thus, PCR amplification is performed by repeatedly subjecting the PCR admixture to a PCR temperature gradient where the gradient includes temperatures where the hybridization, primer extension and denaturation reactions occur. Preferred PCR temperature gradients are from about 35° C. to about 94° C., from about 40° C. to about 94° C., and from about 50° C. to about 94° C.

In preferred embodiments at least about 10, preferably about 10 to 40, cycles of PCR are performed under high stringency conditions using a consensus primer of this invention. With Taq I polymerase, these cycles are generally performed so as to have the following phases: 94° C. for 30 seconds for denaturation, the high stringency annealing temperature for 30 seconds, and 72° C. for 2 minutes for extension. (See Example 2, infra.) Alternatively, other thermostable DNA polymerases can be used, in which case the denaturation, high stringency annealing, and extension temperatures are adjusted according to the thermostability of the particular DNA polymerase. The high stringency annealing temperature is about the melting temperature of the double-stranded DNA formed by annealing, about 35° C. to about 65° C., generally greater than about 55° C., and preferably about 60° C.

In a related embodiment, at least on initial cycle of PCR is conducted under low stringency annealing conditions as a first step, followed by a second step which comprises the thermocycles described above under high stringency conditions. Preferably, the annealing temperature in the second step is greater than the annealing temperature in the first step. The annealing temperature in the second step is lower for shorter primers, because the melting temperature of short double-stranded helices is decreased. Conversely, it is higher for longer primers.

In this two step embodiment, at least one initial cycle of PCR is performed, starting with the at least one consensus primer and the genomic nucleic acids to be amplified. Using Taq I polymerase, the initial cycle(s) of PCR are performed under "low stringency annealing conditions". The term "stringency" refers to the degree of mismatch tolerated during hybridization of the primer and template; the higher the stringency, the less mismatch is tolerated. Preferably, one to five cycles of amplification are performed under these conditions. These cycles are generally performed so as to have the following phases: 94° C. for 5 minutes to denature, 5 minutes at the low stringency annealing temperature, and 72° C. for 5 minutes for extension. More preferably, one to four or one to three low stringency amplification cycles are performed. Most preferred, are one or two low stringency amplification cycles. The low stringency annealing temperature can be from about 30° C. to about 55° C., preferably from about 35° C. to about 55° C., and more preferably from about 40° C. to about 48° C. If mixtures of primers that have considerable sequence homology with the target genome are used, higher temperatures for annealing in the initial cycle(s) can be tolerated, presumably because some of the sequences in the mixtures inevitably anneal quite well to any complex genome and efficiently generate amplification products.

The reaction is performed in a buffer optimized for activity of the particular thermostable DNA polymerase employed. A number of thermostable DNA polymerases have been isolated. See U.S. Pat. No. 4,889,818 describing the thermostable DNA polymerase of *Thermus aquaticus*. In addition, the thermostable DNA polymerases present in any of the thermophilic bacteria is well known and described in U.S. Pat. No. 4,889,818.

The particular CP-PCR conditions employed will depend upon the particular thermostable DNA polymerase used for the amplification reaction and are typically optimized for that particular thermostable DNA polymerase. Effective amounts of the primer(s) and target nucleic acid are admixed in an aqueous PCR buffer that includes an effective amount of an inducing agent, an effective amount of each dNTP. For Taq DNA polymerase, the buffer typically contains an effective amount of Taq, 50 mM KCl, 10 mM Tris-HCl, pH 8.4, 4 mM $MgCl_2$, and 100 $\mu$g/ml gelatin. Each deoxyribonucleoside triphosphate (i.e., A, T, G and C) is typically present at about 0.2 mM concentration when Taq DNA polymerase is used.

The extent to which any particular sequence can be amplified by CP-PCR depends on three general factors: (1) the frequency of priming at flanking sites; (2) the ability of the DNA polymerase used, typically Taq polymerase from *Thermus aquaticus*, to extend the template completely; and (3) the total number of productive cycles.

E. Comparison of the DNA Amplification Products With Those Produced From Known Genomes If the object of the performance of the CP-PCR method is to identify the genome from which the discrete products were produced, the DNA amplification products (fingerprints) obtained from a sample are compared with the amplification products resulting from the performance of CP-PCR on nucleic acids isolated from known genera, species, subspecies and/or strains using the same primer or mixture of primers, in separate reactions.

The samples selected for comparison depend on the expected identification of the test (isolate) organism of unknown genome. In many clinical situations, identification of an organism of an unknown bacterial genome can be narrowed down by means of the site of infection or other clinical factors. For example, the presence of a wound infection may suggest that the test organism is a member of the genus Staphylococcus. If the unknown organism might be Staphylococcus, various species of Staphylococcus could be screened simultaneously as in a panel of preselected DNA samples, such as *S. haemolyticus, S. hominis, S. aureus, S. warneri* and *S. cohnii;* or multiple strains for each species could be used. Similarly, if the unknown organism might be a strain of Streptococcus, the samples selected for comparison are various predetermined and identified strains of Streptococcus. If the unknown organism is a bacterium of enteric origin, various strains of Escherichia, Klebsiella, Enterobacter, Serratia, Salmonella, Shigella, Proteus and Providencia are used. Additional bacterial genera of clinical relevance could also be included in the panel such as a Clostridium or Pseudomonas.

Because the most substantial differences in the CP-PCR amplification products from different bacterial isolates represent differences between species, CP-PCR can be used effectively to reveal a prior misassignment of a strain. Strains that have been assigned to the wrong species are very rapidly uncovered by the CP-PCR method. Typically, when CP-PCR is used to verify the assignment of a bacterial isolate to a species, the primer is chosen to maximize interspecific difference of the discrete DNA amplification products generated by CP-PCR. Primers for this application typically exclude regions substantially complementary to regions of DNA highly conserved between the species being studied.

The comparison between the CP-PCR products of the organism of unknown genome and those produced from known genomes is typically performed by separating the discrete DNA amplification products in an apparatus containing a medium capable of separating DNA fragments by size in order to produce a "fingerprint" of the amplification products as separated bands, and then comparing the fingerprint patterns. The fingerprint patterns are diagnostic of the genus, species, and/or strain to which the test organism of unknown genome belongs. Generally, such separation is carried out by electrophoresis, for example, using gel electrophoresis on agarose or polyacrylamide gels to display the resulting DNA products for visual examination. Many protocols for electrophoresis are known in the art; see U.S. Pat. No. 4,729,947 and B. Perbal, "A Practical Guide to Molecular Cloning," Ch. 9, "Separation of DNA Fragments by Electrophoresis," pp. 340–362, (2d ed., John Wiley & Sons, New York (1988)), incorporated herein by this reference.

Thus, the production of a fingerprint for comparison typically comprises the steps of (1) applying the set of discreet DNA segments produced in a PCR reaction into a channel of the medium in the separating apparatus and (2) separating the discrete DNA segments according to size (size-separating) into bands within the channel to form a fingerprint of the DNA segments characteristic of the genome.

One such representative technique is electrophoresis through 5% polyacrylamide containing 50% urea. The concentration of acrylamide is varied according to the size of the products to be resolved. Commercially available size markers typically derived from the digestion of a plasmid or phage of known sequence with a restriction enzyme are added to the gel.

The individual bands present in the fingerprint are detected by various techniques, such as ethidium bromide staining. At least one of the deoxyribonucleotide triphosphate monomers used in the second stage of the reaction can be radioactive, allowing detection of the bands of the fingerprint by autoradiography, or the primer itself can be radioactively labeled by treatment with an appropriate kinase. Alternatively, fluorescent nucleotides can be incorporated and detection carried out by means of fluorescence.

F. Further Manipulation of Fragments Produced by CP-PCR

Isolated separated fragments can be cleaved with a restriction endonuclease capable of generating polymorphisms, such as TaqI or MspI. Separated fragments produced by CP-PCR and resolved on gels can also be isolated from the gel and reamplified in a conventional PCR procedure to increase the quantity of the isolated band. Isolated fragments can, if desired, be cloned in a bacterial host, typically a strain of *Escherichia coli*, capable of preserving the integrity of any genetically unstable DNA structures such as long, direct and inverted repeats. Such cloned bands then can be sequenced by well-known, conventional techniques, such as the Sanger dideoxynucleotide sequencing technique or the Maxam-Gilbert chemical cleavage sequencing technique.

For many procedures, such as the preparation of DNA probes, it is not necessary either to clone or recut the DNA fragments amplified by CP-PCR and isolated from the gel. Such fragments can be used as probes after further amplification by conventional PCR during which radioactive nucleotides are incorporated in the amplified fragments.

II. APPLICATION TO IDENTIFICATION OF STAPHYLOCOCCUS SPECIES

One significant application of the general method of the present invention is the identification of the species to which an isolate of Staphylococcus belongs. Staphylococcus is a human pathogen and frequently responsible for serious infections occurring in surgical patients. Accordingly, rapid identification of Staphylococcus species is particularly important in a clinical setting.

In the identification of Staphylococcus species by CP-PCR, the discrete DNA amplification products produced from the sample of DNA from the test organism are compared with the DNA amplification products produced from known Staphylococcus species when the same primer is used. We have found between three and twenty products predominate in the CP-PCR products obtained from Staphylococcus genomes. These products are species-specific and can be used to distinguish between *S. haemolyticus, S. hominis, S. aureus, S. warneri* and *S. cohnii.* In some cases, subspecies and/or strains of these species are also distinguished. (See Example 2, infra).

III. APPLICATION TO IDENTIFICATION OF STREPTOCOCCUS STRAINS

In a similar manner, CP-PCR can be used to identify particular strains of Streptococcus. In the identification of Streptococcus strains by CP-PCR, the discrete DNA amplification products produced from the test organism of unknown strain are compared with the DNA amplification products produced from DNA of known Streptococcus strains when the same primer is used. Streptococcus is also an important human pathogen, causing potentially severe infections of the skin and mucous membranes, and its rapid identification is clinically important.

As shown below in Example 2, CP-PCR performed on a number of strains of Streptococcus reveals a fingerprint of amplified bands with some species-specific features, as well as some isolate-specific differences. One can clearly group almost all members of a species based on common bands and group subsets of strains within species based on shared bands that are not present in other strains.

IV. APPLICATION OF CP-PCR TO GENETICS OF EUKARYOTES

The DNA sequences that represent polymorphisms differing from individual to individual of a species obtained from application of the CP-PCR method of the invention are useful in genetic mapping of eukaryotes, including plants such as maize and soybeans, animals, and humans. In particular, CP-PCR can be used to reveal polymorphisms based on the CP-PCR fingerprint. Such polymorphisms are particularly useful for genetic mapping. The polymorphisms generated can be correlated with other markers such as restriction fragment length polymorphisms (RFLPs), which in turn have been linked to genetic markers of known function. A RFLP is a detectable difference in the cleavage pattern of DNA from different individuals of a particular species when that DNA is cleaved with a particular restriction endonuclease. Such differences arises when a mutation affects the sequence cut by the enzyme, removing a site previously present or adding a new site.

CP-PCR can be used to track genetic differences in rice, with a 600-megabase haploid genome (Example 2) and in maize, with a 3000-megabase haploid genome (Example 2). Maize has a genomic complexity comparable to that of the human genome. Similar results are expected with soybeans.

The heterozygosity of the maize genome has been estimated to be about 0.05. Each primer used in the CP-PCR method can probably detect more than one polymorphism between strains at that level of heterozygosity.

Such approaches should allow determination of the linkage distance between polymorphisms and various phenotypes. Phenotypes can be scored in a number of ways, including morphological features and molecular features, such as electrophoretic mobility on proteins and variations in intensity of proteins on two-dimensional gels (Higginbotham et al., "The Genetic Characterization of Inbred Lines of Maize (*Zea mays L.*) Using Two Dimensional Protein Profiles," Symposium, 1990). It is interesting to note that when protein abundance or state of modification is followed as a phenotype, linkage is to the genetic element that causes that variation and often not to the protein being observed. Such genetic element can be a regulator or other control element, or a gene for a modifying enzyme. It is possible, however, to link many protein electrophoretic mobility variants to the CP-PCR map.

A polymorphism can be correlated with a phenotypic character through repeated backcrossing. This introgression method simplifies the background. Comparing the backcrosses with the parents detects polymorphisms linked to the gene of interest.

Another application of the CP-PCR method is in creating a physical CP-PCR map by correlating the recombination frequencies between CP-PCR fragments. By choosing the crosses used in the development of the physical map judiciously, the CP-PCR map will automatically orient itself with respect to the genetic map. Such physical linkage can be studies by pulsed field electrophoresis (PFE). By applying restriction endonucleases making rare cuts, PFE, and Southern blotting to maize or soybean DNA and probing with genetically linked CP-PCR probes, the size of the physical region for large fragments of chromosomes isolated by PFE can be compared with the rate of recombination. Analogous techniques can be employed for mapping the mouse or human genome. This is of interest because recombination is not equal throughout the genome. The CP-PCR method is particularly suitable for this purpose because a great many markers can, in principle, be identified for an area of interest.

The number of individual progeny from crosses that can be inspected and the amount of polymorphism in each marker determines the accuracy with which markers can be mapped. The segregation of polymorphisms revealed by the CP-PCR method in the context of the RFLPs that are already mapped improves the ability to measure genetic distance between them. Computer programs are available for genetic linkage analysis including LIPED (Ott, *Amer. J. Human Genet.* 28:528:529 (1976) for two point linkage analysis, ILINK and CI-LINK from the LINKAGE package (Lathrop et al., *Proc. Natl. Acad. Sci. USA*, 81:3443–3446 (1984); Lathrop et al., *Amer. J. Human Genet.* 37:482–498 (1985)), GMS (Lathrop et al., *Genomics* 2:157–164 (1988)), and MAPMAKER (Lander et al., *Genomics* 1:174–181 (1987)) for multipoint analysis. Additionally, quantitation of the bands allows distinction between homozygotes and heterozygotes for a particular band in the CP-PCR fingerprint.

The use of such linkage analysis techniques allows determination of linkage distance between the polymorphisms and various phenotypes. RFLPs that have been linked to interesting genetic markers can be correlated with the CP-PCR map. For example, tightly linked flanking RFLP markers have been found for the Mdm1 gene on chromosome 6S in maize. This gene is involved in resistance to Maize Dwarf Mosaic Virus (MDMV) (McMullen & Louie, *Mol. Plant-Microbe Interactions* 2, 309 (1989)). Similarly, a RFLP marker less than 1 centiMorgan (cM) from the Htl1 gene, which confers resistance to the fungal pathogen *Helminthosporum turcicum*, has been found (Bentolila et al., Symposium, 1990).

Another approach to mapping makes use of the fact that RFLPs themselves can be generated from CP-PCR fingerprints. For instance, TaqI restriction endonuclease, which recognizes the site TCGA, will cleave CP-PCR products in which there is at least one TaqI site. If a TaqI site is present in one of the CP-PCR fingerprint products in some individuals but not in others, there will be a difference in the fingerprint of TaqI digested DNA from these individuals. This allows the detection of TaqI RFLPs from CP-PCR patterns. Such TaqI RFLPs are among the most common RFLPs known in the genome because the TaqI recognition site contains the hypermutable dinucleotide CpG. Similarly, MspI digests, cut at the recognition site of CCGG, can be used to detect the relatively abundant MspI polymorphisms. Such RFLPs can be either mapped directly in families by genetic mapping or cut out of gels and amplified with radioactively labeled deoxyribonucleoside triphosphates, such as $\alpha$-labeled triphosphates, in conventional PCR to use them to probe Southern blots of the appropriately cleaved human DNAs. To ensure purity, the extracted fragments can be recut with the same enzyme following extraction. Alternatively, the bands isolated from CP-PCR fingerprints can be cloned and sequenced. Preferably, such bands should be cloned in Sure *E. coli* (Stratagene, Cloning Systems, San Diego, Calif.) to preserve the integrity of terminal repeats.

These techniques can also be employed to analyze animal genomes, including the genomes of mice, as well as the human genome. They are particularly useful for filling in the genetic map by linking known markers more precisely.

The CP-PCR method of the invention permits genetic mapping of DNA polymorphisms in mammals without having to first identify RFLP probes. Each polymorphic band in the fingerprint produced by the method represents a heritable characteristic. No clones must be made or plasmids purified. Polymorphisms can be generated by almost any primer selected. The technique requires less than 1/100 of the amount of genomic DNA per lane compared to that needed to prepare a Southern blot for conventional RFLP analysis. The method can use ethidium detection, fluorescent detection or only small amounts of labeled bases relative to Southern hybridization. Moreover, CP-PCR generated DNA polymorphisms can be isolated directly from gels and reamplified to use as probes in "genome walking" or restriction mapping strategies without cloning. Sequencing of some of these polymorphisms will also not require cloning.

One approach for using the CP-PCR method in human genetics can produce products assignable to the human fragment in a somatic cell hybrid. As long as the recipient is the same for a set of hybrids, the products that will be different from a non-hybrid control CP-PCR will be the human fragments. Such bands would assign the human fragment on the genetic map if the band was already genetically assigned. Also, such bands can be isolated from the gel and used to make a DNA probe.

V. COMPOSITIONS AND KITS

Many of the reagents described herein (e.g., nucleic acids such as primers, vectors, and the like) have a number of forms, particularly variably protonated forms, and in equilibrium with each other. As the skilled practitioner will understand, representation herein of one form of a compound or reagent is intended to include all forms thereof that are in equilibrium with each other.

The reagents described herein can be packaged in kit form. As used herein, the term "package" refers to a solid matrix or material customarily utilized in such a kit system in the form of an enclosure that is capable of holding within fixed limits one or more of the reagent components for use in a method of the present invention. Such materials include glass and plastic (e.g., polyethylene, polypropylene and polycarbonate) bottles, vials, paper, plastic and plastic-foil laminated envelopes and the like. Thus, for example, a package can be a glass vial used to contain the appropriate quantities of polynucleotide primer(s), genomic DNA, vectors, restriction enzyme(s), DNA polymerase, DNA ligase, or a combination thereof. An aliquot of each component sufficient to perform at least one PCR thermocycle will be provided in each container.

Kits useful for producing a primer extension product for amplification of a specific nucleic acid sequence using a primer extension reaction methodology also typically include, in separate containers within the kit, dNTPs where N is adenine, thymine, guanine and cytosine, and other like agents for performing primer extension reactions.

The reagent species of any system described herein can be provided in solution, as a liquid dispersion or as a substantially dry powder, e.g., the primers may be provided in lyophilized form.

In one embodiment, the present invention contemplates a kit for typing an isolate of organism comprising an enclosure containing, in separate containers, at least on consensus primer, preferably a structural RNA consensus primer, and at least one genomic DNA sample for use as a control in a typing method of this invention. In preferred embodiments, a panel of genomic DNA samples derived from predetermined species are included, as described herein. The consensus primers and the genomic DNA for use in a kit for typing an isolate of organism are comprised as previously described.

The kit can further contain, in one or more separate enclosures, one or more panels of genomic DNA representative of groups of species, combined in a manner to allow comparison of subspecies within a species, of species within a genus, of genera within families, and the like, for determining the location of an isolate organism on the evolutionary scale.

In order that the invention described herein may be more fully understood, the following examples are set forth. It should be understood that the following examples are for illustrative purposes only and are not to be construed as limiting the invention.

EXAMPLES

1. Isolation of DNA for CP-PCR

Strains of Staphylococcus listed in Table 2 were grown overnight at 37° C. in 2–5 ml of brain heart infusion media. The cells were pelleted, resuspended in 0.2 ml of TE (0.01M Tris-HCl, pH 8.0, 1 mM EDTA) with 0.2 mg/ml lysostaphin and incubated at 37° C. for one hour. Following this incubation, 0.2 ml proteinase K solution (containing 0.5 mg/ml proteinase K, 1% Sarkosyl, 200 mM EDTA, and 1 mM calcium chloride) was added to each sample. The samples were then digested at 50° C. for one hour. The clear lysates were extracted with phenol and then chloroform; the DNA was then precipitated with ethanol. The precipitated DNA was dissolved in TE, and its final concentration was estimated by agarose gel electrophoresis and ethidium bromide staining.

TABLE 2

| Strains and Species Analyzed by CP-PCR | | | |
|---|---|---|---|
| Species | Primer | Figure | Lane |
| Staphylococcus | | | |
| S. haemolyticus 29970 | T5A + T3A | 2 | 20 |
| S. haemolyticus CC 12J2 | T5A + T3A | 2 | 21 |
| " | T5A | 1 | 1 |
| " | T3A | 1 | 6 |
| " | T5A + T3A | 1 | 11 |
| S. haemolyticus PAY 9F2 | T5A + T3A | 2 | 22 |
| S. haemolyticus AW 263 | T5A + T3A | 2 | 23 |
| S. haemolyticus MID 563 | T5A + T3A | 2 | 24 |
| S. hominis 27844 | T5A | 1 | 2 |
| " | T3A | 1 | 7 |
| " | T5A + T3A | 1 | 12 |
| " | T5A + T3A | 2 | 25 |
| S. hominis 27846 | T5A + T3A | 2 | 26 |
| S. warneri CPB10E2 | T5A + T3A | 2 | 27 |
| " | T5A | 1 | 3 |
| " | T3A | 1 | 8 |

TABLE 2-continued

| Strains and Species Analyzed by CP-PCR | | | |
|---|---|---|---|
| Species | Primer | Figure | Lane |
| " | T5A + T3A | 1 | 13 |
| S. warneri GAD473 | T5A + T3A | 2 | 28 |
| S. warneri MCY3E6 | T5A + T3A | 2 | 29 |
| S. warneri PBNZP4D3 | T5A + T3A | 2 | 30 |
| S. aureus ISP8 | T5A + T3A | 2 | 31 |
| " | T5A | 1 | 5 |
| " | T3A | 1 | 9 |
| " | T5A + T3A | 1 | 14 |
| " | T5A + T3A | 3 | 12 |
| " | T5B + T3A | 3 | 14 |
| S. aureus 8432 | T5A + T3A | 2 | 32 |
| aureus 15564 | T5A + T3A | 2 | 33 |
| S. aureus 6538 | T5A + T3A | 2 | 34 |
| S. aureus 3A | T5A + T3A | 2 | 35 |
| " | T5A + T3A | 3 | 13 |
| " | T5B + T3A | 3 | 15 |
| S. aureus 12600 | T5A + T3A | 2 | 36 |
| S. cohnii JL143 | T5A + T3A | 2 | 37 |
| " | T5A | 1 | 4 |
| " | T3A | 1 | 10 |
| " | T5A + T3A | 1 | 15 |
| S. cohnii CM 89 | T5A + T3A | 2 | 38 |
| S. cohnii SS 521 | T5A + T3A | 2 | 39 |
| S. cohnii 29974 | T5A + T3A | 2 | 40 |
| Streptococcus (serotype) | | | |
| S. pyogenes (A) D471 | T5A + T3A | 2 | 1 |
| " | T5A + T3A | 3 | 16 |
| " | T5B + T3A | 3 | 18 |
| S. pyogenes (A) Ti/195/2 | T5A + T3A | 2 | 2 |
| " | T5A + T3A | 3 | 17 |
| " | T5B + T3A | 3 | 19 |
| S. pyogenes (A) 40 RS 15 | T5A + T3A | 2 | 3 |
| S. pyogenes (A) 52 RS 15 | T5A + T3A | 2 | 4 |
| S. pyogenes (A) 47 RS 15 | T5A + T3A | 2 | 5 |
| S. pyogenes (A) 55 RS 15 | T5A + T3A | 2 | 6 |
| S. pyogenes (G) T28/51/4 | T5A + T3A | 2 | 7 |
| S. pyogenes (A?) K58 Hg | T5A + T3A | 2 | 8 |
| S. pyogenes (A) UAB 098 | T5A + T3A | 2 | 9 |
| S. pyogenes (A) UAB 097 | T5A + T3A | 2 | 10 |
| S. pyogenes (A) 14RP81 | T5A + T3A | 2 | 11 |
| S. pyogenes (A) D471Rot | T5A + T3A | 2 | 12 |
| S. pyogenes (G) 1/E9 | T5A + T3A | 2 | 13 |
| S. pyogenes (G) 040/011 | T5A + T3A | 2 | 14 |
| S. mutans T8 | T5A + T3A | 2 | 15 |
| S. pyogenes (B) 50316 | T5A + T3A | 2 | 16 |
| S. pyogenes (A) UAB 092 | T5A + T3A | 2 | 17 |
| Enterococcus | | | |
| E. faecalis, OGI X | T5A + T3A | 2 | 18 |
| E. faecalis, JH2-2 | T5A + T3A | 2 | 19 |
| Maize (Zea Maize) B73 | T5A + T3A | 3 | 1 |
| " | T5B + T3A | 3 | 3 |
| Maize Mo17 | T5A + T3A | 3 | 2 |
| Human (Homo sapien) 584 | T5A + T3A | 3 | 8 |
| " | T5B + T3A | 3 | 10 |
| Human 694 | T5A + T3A | 3 | 9 |
| " | T5B + T3A | 3 | 11 |
| Rice (Oryza sativa) G1 | T5A + T3A | 3 | 4 |
| " | T5B + T3A | 3 | 6 |
| Rice G2 | T5A + T3A | 3 | 5 |
| " | T5B + T3A | 3 | 7 |

All Staphylococcus strains shown in Table 2 were kindly provided by W. E. Kloos of North Carolina State University except ISP-8 from Peter Pattee, (Iowa State University, Ames, Iowa) and those from the American Type Culture Collection designated by the four or five digit numerals. Other abbreviations are arbitrary designations for laboratory strains.

DNAs from the human pathogenic strains of Streptococcus pyogenes, S. mutans and Enterococcus faecalis were all kindly supplied by Susan Hollingshead (Univ. of Alabama, Birmingham, Ala.).

Total genomic DNA from maize and rice strains were kindly provided by Rhonda Honeycutt, (Iowa State U., Ames Iowa). Human DNAs from normal intestines were kindly provided by Manuel Perucho (CIBR, Calif.).

Genomic DNA was isolated from the other species shown in Table 2 by the same detergent lysis and phenol extraction protocol described above.

2. Performance of CP-PCR Amplification

Primers described in Table 1 were chemically synthesized and obtained from Genosys, (Houston, Tex.).

PCR reaction admixtures were prepared in a volume of 50 μL containing 1×Taq polymerase buffer (Stratagene Cloning Systems, San Diego) adjusted to 4 mM with $MgCl_2$, 0.2 mM of each deoxyribonucleotide triphosphate, 1.25 units Taq polymerase, 1 uM consensus primer (or primers), 50 uCi alpha [32P] dCTP, and template DNA at various quantities from 100 ng to 3.2 ng as indicated. The reactions were overlaid with oil and cycled forty times through the following temperature profile: 94° C. for 30 seconds for denaturation, 50° C. for thirty seconds for annealing of primer, and 72° C. for two minutes for extension. The results of this set of PCR cycles was the formation of a discrete set of amplified DNA segments (primer extension products). The resulting products were resolved by electrophoresis in 1X TBE through 5% Acrylamide-50% Urea and visualized by autoradiography using Kodak X-Omat TM AR film with an intensifying screen at −70° C. for 6 hours.

The results, shown in FIG. 1, indicate that reproducible fingerprints can be obtained over a 25-fold range of template concentration at 50° C. Other experiments, not shown, indicated that the fingerprint did not vary when the low stringency annealing step was varied between 45° C. and 50° C. which is suitable for partly mismatched primers. Suitable temperatures probably range from 40° C. to 55° C.

There were a number of products generated for each genome in FIG. 1 whether T5A and T3A were used alone or together, indicating PCR initiated at a variety of places in the genome, as expected. With the exception of *S. cohnii*, which was already known to be the most divergent species within the genus, the CP-PCR patterns were very similar between the species, indicating that the tRNA gene clusters probably evolve relatively slowly. This is in contrast to arbitrarily primed (AP)-PCR, Welsh et al, *Nucleic Acids Res.*, 18: 7213-7218 (1990), or total genome restriction digestion, Cinco et al, *FEMS Microbiol. Immunol.*, 47: 511-514 (1989), that give very different patterns when different species are compared.

A survey was performed on forty strains of bacteria, representing many strains from five species of Staphylococcus, four species of Streptococcus and a species of Enterococcus. The organization of the tRNA genes in these species has not been described, but they are presumably similar to those of other related bacteria, such as Bacillus. FIG. 2 shows that within a species there was generally no variation in the CP-PCR pattern. There were only two exceptions. A Streptococcus pyogenes strain K58Hg that was designated serotype A (lane 8) gave a pattern identical to serotype b (lanes 7, 13 and 14). Interestingly, AP-PCR experiments group this strain with serotype b and not serotype a. It is likely that K58Hg is in fact a serotype b. The other exception was a strain of *S. haemolyticus* (lane 20) that was obtained from the ATCC. Although not explained, preliminary data indicates that *S. haemolyticus* consists of at least two groups of strains that are rather divergent and may in fact be different species.

Figure 3:
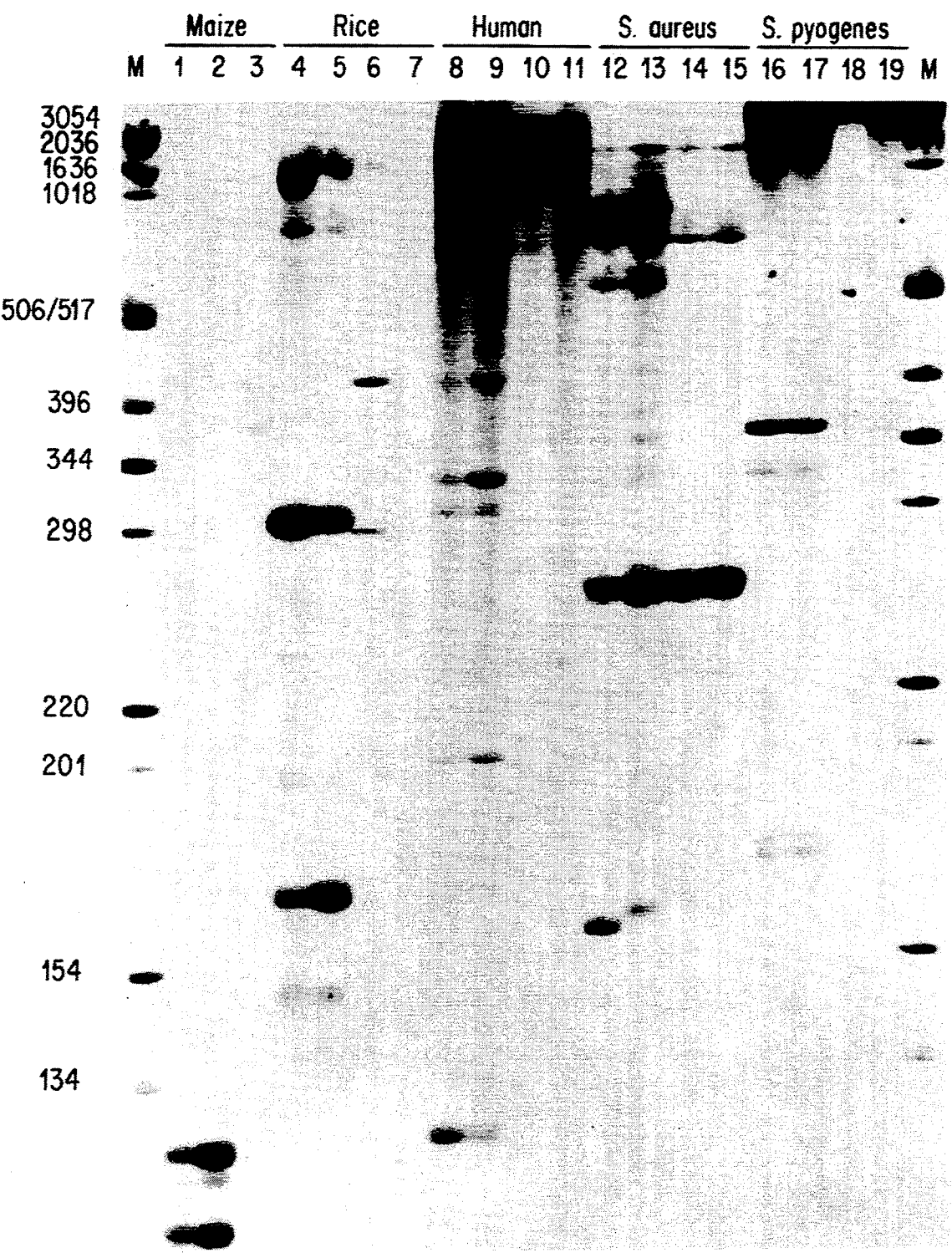
FIG. 3 shows the CP-PCR patterns produced by using genomes from species across the three kingdoms and illustrates the existence of polymorphisms, as described in Example 2. The reaction was performed using 50 ng of template under the standard PCR conditions. The low temperature annealing step was 50° C. Lanes 1 to 9 used the primers T5A and T3A. Lanes 10 to 19 used T5B and T3A. See Table 1 for the strains used in each lane.

CP-PCR should work for a wide variety of species because tRNA genes are highly conserved, are abundant, and are generally arranged in clusters. FIG. 3 shows CP-PCR reactions on the genomes of species from three kingdoms. In addition to the bacterial genomes, there were fingerprints generated for the maize, rice and human genomes with at least one of the two pairs of primers tested. For example, the rice fingerprints are identical between strains, but the T5A/T3A pair of primers (lanes 4 and 5) gives a completely different pattern than the T5B/T3A pair (lanes 6 and 7).

In the case of eukaryotes, a typical consensus tRNA primer will prime both nuclear and organelle (mitochondrial and chloroplast) tRNA genes. Plant mitochondrial and chloroplast genomes do not seem to have a high rate of point mutation, however, the evolution of animal mitochondrial genomes is fast. In this latter case, it can be expected that the resulting CP-PCR products will vary over a shorter evolutionary time than nuclear products.

Organelle genomes, despite their small size, can contribute up to half of the DNA in the cell, due to their high copy number. Nevertheless, for CP-PCR the best matches with the primer are probably more important than copy number and these best matches will generally be to nuclear genes because the number of different nuclear tRNA gene sequences greatly exceeds the number of different organelle tRNA gene sequences.

The data does not clearly prove that the CP-PCR products shown are, in fact, from tRNA genes nor, in the case of eukaryotes, if they are from the nuclear or organelle genomes. However, the patterns were identical between divergent individuals within each species. Regardless of the origin of the pattern, CP-PCR is a useful method of species classification. The consistency of the patterns between bacterial species is strong evidence that the fingerprints are not generated by arbitrarily primed-PCR. Such AP-PCR fingerprints are not conserved between species.

The results in FIGS. 1-3 indicate that consensus tRNA gene primers that amplify the region between tRNA genes can be used to generate PCR fingerprints that are generally invariant between strains of the same species and are often substantially conserved between related species. This property makes the method applicable to the identification of organisms by a genome based method that is independent of other criteria such as morphology. The ease with which the method can be performed, independent of the genome size, sequence, concentration of genomic DNA, or the cycling parameters, indicates that it is the method of choice when examining a large number of different strains for which a rapid and convenient method for categorization is desired.

While there are many ways to determine species and genus, CP-PCR using consensus tRNA primers is a simple and fast method that complements those that already exist and has the virtue that the polymorphisms measured are not themselves likely to be selected. They are, potentially, more likely to be near neutral than other characters such as nutrition and perhaps less likely to result from convergent evolution, which is a drawback of classification by morphological criteria. It is also an advantage that the data is collected for regions scattered throughout the genome rather than from sequence differences in a single location that may not reflect the whole genome. A single CP-PCR fingerprint will generally have less information than comparing the DNA sequence of a specific region in each organism. However, CP-PCR is less technically demanding and less time consuming than DNA sequencing. CP-PCR could be a method of choice when large number of individuals are to be screened or as a first step when identifying species based on genomic sequence. Since data acquisition is trivial in CP-PCR, the number of consensus primers and thus the number of patterns that can be generated is large. Any required number of different fingerprints could be generated to provide the necessary markers for species classification. Furthermore, as demonstrated, primers that produce fingerprints from the genomes of a wide variety of organisms can be devised by the present methods. Thus, organisms one essentially knows nothing about can immediately be examined. In addition, it is possible to develop tRNA consensus primers that are targeted preferably to a particular kingdom or to either the nuclear genome or organelle genomes of eukaryotes.

The method presented represents the simplest available universal way to reliably compare genomes of organisms at the species/genus level. The method has applications in ecology and epidemiology.

ADVANTAGES OF THE INVENTION

The present invention provides a method with several advantages for identification of bacteria and other biological materials. The method is simple to perform and rapid; results can be obtained in as little as 36 hours when the template nucleic acids are isolated by boiling. Only small samples of material, e.g., nanogram amounts, are needed. The method yields information that allows the differentiation of even closely related species and can be extended to differentiate between subspecies or strains of the same species. The method requires no prior knowledge of any biochemical characteristics, including the nucleotide sequence of the target nucleic acids, of the organism to be identified. Initially, it requires the use of no species-specific reagents, because the primer used is based on consensus sequences as described herein.

Additionally, the method possesses the important advantage of requiring only one primer sequence for amplification although two or more primers can be used in some embodiments.

The CP-PCR method of the invention can be used to provide identification of other types of organisms, including viruses, fungi, mammals and plants. The method also provides an efficient way of generating polymorphisms for use in genetic mapping, especially of eukaryotes, including animals, particularly mice and humans. This method has many applications in mammalian population genetics, pathology, epidemiology and forensics.

Although the present invention has been described in considerable detail with regard to certain preferred versions thereof, other versions are possible. Therefore, the spirit and scope of the appended claims should not be limited to the descriptions of the preferred version contained herein.

---

What is claimed is:

1. A method of generating a set of discrete DNA segments characteristic of a genome comprising:
   (a) forming a polymerase chain reaction (PCR) admixture by combining, in a PCR buffer, genomic DNA and at least one structural RNA consensus primer from about 10 to about 50 nucleotide bases in length;
   (b) subjecting said PCR admixture of step (a) to a plurality of PCR thermocycles to produce a plurality of DNA segments, thereby forming a set of discrete DNA segments, wherein said consensus primer is a tRNA consensus primer selected from the group consisting of:
   (T5A)   5'-AGTCCGGTGCTCTAACCAACTGAG-3' (SEQ ID NO:1),
   (T5B)   5'-AATGCTCTACCAACTGAACT-3' (SEQ ID NO:2),
   (T3A)   5'-GGGGGTTCGAATTCCCGCCGGCCCCA-3' (SEQ ID NO:3), and
   (T3B)   5'-AGGTCGCGGGTTCGAATCC-3' (SEQ ID NO:4).

2. A method for typing an organism having genomic DNA, which method comprises:
   (a) forming a polymerase chain reaction (PCR) admixture by combining, in a PCR buffer, said genomic DNA and at least one structural RNA consensus primer from about 10 to about 50 nucleotide bases in length;
   (b) subjecting said PCR admixture of step (a) to a plurality of PCR thermocycles to produce a plurality of DNA segments, thereby forming a set of discrete DNA segments,
   (c) applying the set of discrete DNA segments produced in step (b) to a channel of a separating apparatus;
   (d) size-separating the applied segments into bands within the channel to form a fingerprint of segments characteristic of said genome,
   (e) comparing the fingerprint of step (d) with the fingerprints for control samples of genomic DNA from a panel of predetermined species of organisms prepared in accordance with steps (a)–(d), and recording the results of the comparison, wherein said consensus primer is a tRNA consensus primer selected from the group consisting of:
   (T5A)   5'-AGTCCGGTGCTCTAACCAACTGAG-3' (SEQ ID NO:1),
   (T5B)   5'-AATGCTCTACCAACTGAACT-3' (SEQ ID NO:2),
   (T3A)   5'-GGGGGTTCGAATTCCCGCCGGCCCCA-3' (SEQ ID NO:3), and
   (T3B)   5'-AGGTCGCGGGTTCGAATCC-3' (SEQ ID NO:4).

3. A consensus primer wherein said primer has a nucleotide sequence selected from the group consisting of:
   (T5A)   5'-AGTCCGGTGCTCTAACCAACTGAG-3' (SEQ ID NO:1),
   (T5B)   5'-AATGCTCTACCAACTGAACT-3' (SEQ ID NO:2),
   (T3A)   5'-GGGGGTTCGAATTCCCGCCGGCCCCA-3' (SEQ ID NO:3), and
   (T3B)   5'-AGGTCGCGGGTTCGAATCC-3' (SEQ ID NO:4).

4. A kit for typing an organism, said kit comprising an enclosure containing, in separate containers, at least one structural RNA consensus primer and at least a sample of isolated genomic DNA from a panel of species of organisms wherein said structural RNA consensus primer is a tRNA consensus primer selected from the group consisting of:

(T5A) 5'-AGTCCGGTGCTCTAACCAACTGAG-3' (SEQ ID NO:1),
(T5B) 5'-AATGCTCTACCAACTGAACT-3' (SEQ ID NO:2),
(T3A) 5'-GGGGGTTCGAATTCCCGCCGGCCCCA-3' (SEQ ID NO:3),
and
(T3B) 5'-AGGTCGCGGGTTCGAATCC-3' (SEQ ID NO:4).

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:1:

AGTCCGGTGC TCTAACCAAC TGAG    24

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: tRNA ( i i i ) HYPOTHETICAL: NO ( i v ) ANTI-SENSE: NO ( x i ) SEQUENCE DESCRIPTION: SEQ ID NO:2:

AATGCTCTAC CAACTGAACT    20

(2) INFORMATION FOR SEQ ID NO:3:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:3:

GGGGGTTCGA ATTCCCGCCG GCCCCA     26

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: tRNA (iii) HYPOTHETICAL: NO (iv) ANTI-SENSE: NO (xi) SEQUENCE DESCRIPTION: SEQ ID NO:4:

AGGTCGCGGG TTCGAATCC     19